United States Patent [19]

Forster

[11] Patent Number: 4,584,867
[45] Date of Patent: Apr. 29, 1986

[54] DEVICE FOR SELECTIVELY DETERMINING THE COMPONENTS OF GAS MIXTURES BY MEANS OF A GAS SENSOR

[75] Inventor: Martin Forster, Jona, Switzerland

[73] Assignee: Cerberus AG, Männedorf, Switzerland

[21] Appl. No.: 640,125

[22] Filed: Aug. 3, 1984

[30] Foreign Application Priority Data

Aug. 30, 1983 [CH] Switzerland .................. 4736/83

[51] Int. Cl.⁴ .................................... G01N 27/12
[52] U.S. Cl. ............................................ 73/23
[58] Field of Search ............. 73/23, 27 R; 338/34; 340/634; 422/98

[56] References Cited

U.S. PATENT DOCUMENTS

| | | | |
|---|---|---|---|
| 3,695,848 | 10/1972 | Taguchi | 73/27 R |
| 3,714,562 | 1/1973 | McNerney | 73/27 R |
| 3,831,432 | 8/1974 | Cox | 73/23 |
| 4,164,862 | 8/1979 | Jackson . | |
| 4,453,397 | 6/1984 | Ohta et al. | 73/23 |
| 4,457,161 | 7/1984 | Iwanaga et al. | 73/23 |

FOREIGN PATENT DOCUMENTS

2098575 3/1972 France .

OTHER PUBLICATIONS

Publication by H. Arima et al entitled: "New City Gas Detector Using a Thick Film Hybrid Sensor", in 32nd Electronic Components Conference, May 10–12, 1982, San Diego, Calif., pp. 290–295.
Patents Abstracts of Japan, vol. 6, No. 141, (p. 131) [1019] Jul. 30, 1982.

*Primary Examiner*—Stephen A. Kreitman
*Attorney, Agent, or Firm*—Werner W. Kleeman

[57] ABSTRACT

The device comprises a gas sensor containing a predetermined number of sensor elements which change their electric conductivity under the action of gases. Such a gas sensor is used for selectively determining the components of gas mixtures. For this purpose the individual sensor elements are arranged on a heat-resistant, thermally insulating substrate and the individual sensor elements are sensitized for the determination of different components of the gas mixture by selecting different materials and/or operating temperatures for the individual sensor elements. The sensor elements and its components are arranged such that the gas mixture to be investigated is guided past the sensor elments in a directed flow. The temperatures of the sensor elements increase in a stepwise manner in the direction of the gas flow and thereby a further increase in the selectivity of the gas sensor is achieved.

31 Claims, 9 Drawing Figures

DEVICE FOR SELECTIVELY DETERMINING THE COMPONENTS OF GAS MIXTURES BY MEANS OF A GAS SENSOR

CROSS-REFERENCES TO RELATED APPLICATIONS

This application is related to (i) the commonly assigned, copending U.S. application Ser. No. 06/586,329, filed March 5, 1984, entitled "DEVICE FOR THE DETECTION OF GASEOUS IMPURITIES IN AIR BY MEANS OF A GAS SENSOR"; (ii) the commonly assigned, copending U.S. application Ser. No. 06/590,230, filed Mar. 16, 1984, entitled "GAS DETECTION DEVICE HAVING A SENSOR COMPRISING AT LEAST ONE METAL OXIDE"; (iii) the commonly assigned, copending U.S. application Ser. No. 06/635,881, filed July 30, 1984, entitled "DEVICE FOR DETECTING GASEOUS CONTAMINANTS IN AIR BY MEANS OF A GAS SENSOR AND METHOD OF PRODUCING SUCH GAS SENSOR"; and (iv) the commonly assigned, copending U.S. application Ser. No. 06/633,652, filed July 23, 1984, entitled "METHOD OF PRODUCING CONSTITUENT MATERIALS FOR GAS SENSORS".

BACKGROUND OF THE INVENTION

The present invention relates to a new and improved device for selectively determining the components of gas mixtures by means of a gas sensor containing a predetermined number of sensor elements which change their electric conductivity under the action of the components of the mixture to be determined and further containing an evaluation device or circuit arrangement.

A gas sensor of this type has been presented at the 32nd Electronic Components Conference which was held at San Diego, Calif., from May 10 to May 12, 1982.

Gas sensors have been used for some time for different purposes like, for example, environmental protection, garage monitoring, fire protection and explosion protection. For this purpose inexpensive sensors are utilized which are made of metal oxides having an electric conductivity which depends on the concentration of the gases to be detected in the ambient air. The concentration of the gas to be detected can be derived from the variation in the electric conductivity. In order to carry out the gas detection with such sensors the sensor must be brought to a temperature of about 450° C. The known gas sensors are made of a finely ground metal oxide powder sintered to a carrier or substrate which is provided with electrodes. Such gas sensors exhibit only very little selectivity in their gas detection properties. The measured values obtained by using these gas sensors do not permit any conclusion with respect to which component in a gas mixture has been detected.

The individual components of gas mixtures cause widely different changes in the conductivity of the gas sensors, i.e. the gas sensors have different sensitivities with respect to the components of the gas mixture. It is therefore desirable to obtain data about the kind of gas to which the gas sensor responds. It is important, for example, for the supply of city gas or natural gas to residential areas that the exit of gas at leakage locations and toxic carbon monoxide which is formed by incomplete combustion processes are rapidly and reliably detected. Ethanol vapor represents a frequently interfering gas in such cases and frequently occurs, for to the effect that the gas sensors which are sensitive to carbon monoxide and hydrocarbons also respond to ethanol vapor.

Therefore, at the initially mentioned 32nd Electronic Component Conference a gas sensor has been suggested in which three gas sensors are provided which consist of different constituent materials. Two of the gas sensors serve for the detection of methane which is the main component in natural gas and for the detection of hydrogen and/or carbon monoxide which are components of city gas or coal or are formed by incomplete combustion. Since the two sensor elements of the two gas sensors also respond to ethanol vapor which represents the interfering gas, the concentration of ethanol vapor is measured by means of a third gas sensor which specifically reacts to ethanol vapor. The measured value determined by the third gas sensor is accounted for in determining the concentrations of methane and carbon monoxide by means of the other two sensor elements or gas sensors. Such gas detector, however, has the disadvantage that it responds only to two components of gas mixtures while a further specific component can be excluded as an interfering factor.

SUMMARY OF THE INVENTION

Therefore, with the foregoing in mind, it is a primary object of the present invention to provide a new and improved device for selectively determining components of gas mixtures by means of a gas sensor which avoids the aforementioned drawbacks and limitations of the prior art gas sensors heretofore discussed.

Another and more specific object of the present invention is directed to the provision of a new and improved device for selectively determining the components of gas mixtures by means of a gas sensor which has a highly improved selectivity in the determination of a larger number of components contained in a gas mixture.

Now in order to implement these and still further objects of the invention, which will become more readily apparent as the description proceeds, the device of the present development is manifested by the features that, the sensor elements are arranged on a heat-resistant, thermally insulating substrate and the individual sensor elements are provided for the determination of different components of gas mixtures due to the selection of their constituent material and/or their operating temperature.

In a preferred embodiment of the device according to the invention the sensor elements and the eventually present heating devices are arranged in such a manner that the gas mixture to be investigated is guided in a directed flow past the sensor elements.

In a particularly preferred embodiment of the inventive device a gas-impervious layer is provided to guide the gas mixture to be investigated such that the gas mixture preferably passes the sensor elements one after the other.

In a further structure of the inventive device the sensor elements have different operating temperatures and preferably a sensor element which is forwardly positioned with respect to the direction of the gas flow has a lower operating temperature than the sensor element which is positioned rearwardly thereof.

The sensor elements also can be arranged such as to form a coherent block and to form a temperature gradient in the direction of the gas flow, i.e. the temperature gradually increases in the direction of the gas flow. Electrodes are series-arranged at the block of sensor elements and different electrodes correspond to different temperature regions. Different gases are detected at the differently heated regions of the block of sensor elements and the changes in conductivity are signalled to the evaluation device or circuit arrangement by the related electrodes.

BRIEF DESCRIPTION OF THE DRAWINGS

The invention will be better understood and objects other than those set forth above, will become apparent when consideration is given to the following detailed description thereof. Such description makes reference to the annexed drawings wherein throughout the various figures of the drawings there have been generally used the same reference characters to denote the same or analogous components and wherein.

DETAILED DESCRIPTION OF THE PREFERRED EMBODIMENTS

Describing now the drawings, it is to be understood that only enough of the construction of the device has been shown as needed for those skilled in the art to readily understand the underlying principles and concepts of the present development, while simplifying the showing of the drawing. The sensor elements 5 of the gas sensors 6 used in the different embodiments of the inventive device are produced from a constituent material 1 which is obtained by a method fully described in the initially cross-referenced, copending U.S. application Ser. No. 06/635,881, filed July 30, 1984, entitled "DEVICE FOR DETECTING GASEOUS CONTAMINANTS IN AIR BY MEANS OF A GAS SENSOR AND METHOD OF PRODUCING SUCH GAS SENSOR" and in the initially cross-referenced, copending U.S. application Ser. No. 06/633,652, filed July 23, 1984, entitled "METHOD OF PRODUCING CONSTITUENT MATERIALS FOR GAS SENSORS". This constituent material is also commercially available.

Figure 1:
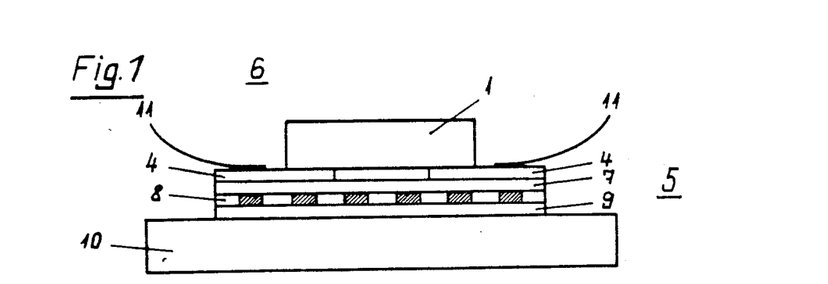
FIG. 1 is a section through a gas sensor used in a first embodiment of the device according to the invention.

FIG. 1 is a cross-section through a gas sensor 6 used in a first embodiment of the device according to the invention. The cross-section through the gas sensor 6 is at a location at which a sensor element 5 is arranged. The gas sensor 6 comprises a predetermined number of such sensor elements 5. The constituent material 1 which changes its electric conductivity under the action of gases is connected at its ends to a related one of two electrodes 4 which are connected to an evaluation device or circuit arrangement 100 (FIG. 2) by electric conductors 11. A heating device 8 is located below the constituent material 1 and is arranged between a first electrically insulating layer 7 and a second electrically insulating layer 9. The heating device 8 may be constituted by conventional heating wires. The heating device 8 may also comprise a platinum layer, an iridium layer or a layer made of a platinum-iridium alloy all of which have a large temperature coefficient of the electric conductivity. In temperature by measuring the resistance of the heating device 8. The constituent material 1 of the sensor element 5 is heated to a predetermined operating temperature by the heating device 8. The individual sensor elements 5 are arranged on a heat-resistant, thermally insulating, substrate 10 and together form the gas sensor 6. The gas sensor 6 can be placed in a suitable housing which is not particularly illustrated and which is attached at the location to be monitored.

The heating device 8 is connected to an appropriate current source by supply lines which are not shown. There are present in the evaluation device or circuit arrangement 100 switching elements by means of which there are adjusted and maintained constant predetermined operating temperatures which may be in the range of room temperature to about 450° C. The different sensor elements 5 which may be composed of the same or different constituent materials 1 can be adjusted to the same operating temperature; however, in order to detect different components of gas mixtures each one of the sensor elements 5 may be heated to a different operating temperature within the range as mentioned hereinbefore.

In order to keep the current consumption of the gas sensor 6 as low as possible the dimensions of its components are kept as small as possible. Contrary to the prior art gas sensors, the sensor elements 5 are not suspended from the supply lines but are located on a solid, heat-resistant and thermally insulating substrate 10. Therefore, the supply lines can have a very small cross-section. For example, a diameter of 30 μm is completely sufficient, whereby the heat dissipation is further reduced. The spatial dimensions of the gas sensor 6 shown at FIG. 1 are 5 mm in height, 3 mm in width and 3 mm in length. Due to such extremely small dimensions the gas sensors 6 can also be mounted at difficultly accessible locations.

Assuming that only one dangerous gas occurs, there is not required the presence of a number of sensor elements 5. In this case a single sensor element 5 suffices and which is arranged conjointly with its heating device 8 which is located between the first and second electrically insulating layers 7 and 9 on a heat-resistant, thermally insulating substrate 10. The heating device 8 heats the constituent material 1 of the gas sensor 6 to a temperature which is optimally adapted to the detection of the one dangerous gas. Due to the use of the thermally insulating substrate 10 there is obtained a very economical operation of such embodiment of the inventive device including the gas sensor 6 since only a low heating power is required which amounts to only about 300 mW at a temperature of the constituent material 1 of about 360° C.

Figure 2:
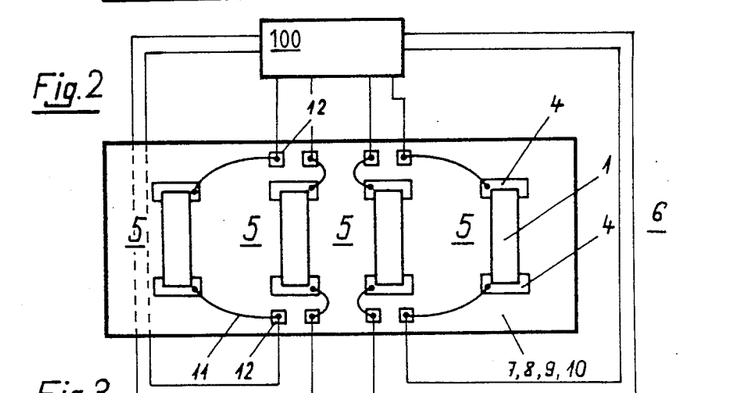
FIG. 2 is a top plan view of the gas sensor shown in FIG. 1.

FIG. 2 shows a top plan view of the gas sensor 6 which has been shown in cross-section in FIG. 1. The electric conductors 11 of the electrodes 4 are led to contact points 12 mounted to the first electrically insulating layer 7. The electric contact points 12 are connected to the evaluation device or circuit arrangement 100 by not particularly designated connecting wires or leads. The evaluation device or circuit arrangement 100 measures the changes in conductivity and indicates the detected gas and its concentration. This conventional evaluation device or circuit arrangement 100 is not subject of the present invention and therefore is merely schematically indicated in FIG. 2. As previously indicated, the evaluation device or circuit arrangement 100 contains switching elements by means of which all of the sensor elements 5 can be heated to the same operating temperature or to different operating temperatures. It is also possible to operate all of the sensor elements 5 at room temperature. In that case the heating device 8 and the first and second electrically insulating layers 7 and 9 may be omitted.

Under the action of a gas mixture acting on the sensor elements 5 in the gas sensor 6 the electric conductivities of the individual sensor elements 5 change in dependence on the concentration of the components in the gas mixture. The sensitivity of each one of the individual sensor elements 5 is adjusted to a different component of the gas mixture by selecting the constituent material 1 and/or the operating temperature of the sensor elements 5. Depending on the composition of the gas mixture to be investigated the constituent materials 1 and the operating temperatures of the sensor elements 5 are adjusted such that good selectivity is ensured for the different components. The changes in the electric conductivity which occur at the electrodes 4 are measured by the evaluation device or circuit arrangement 100 via the electric conductors 11, the contact points 12 and the connecting wires.

The number of sensor elements 5 in the gas sensor 6 is a function of the number of components to be determined in the gas mixture. For example, the device illustrated in Figure 2 is suited for detecting four different components.

In a specific example of this particular embodiment of the inventive device the sensor element on the left-hand end 0.1% platinum and this sensor element is heated to an operating temperature of about 360° C. Under these conditions hydrogen is detected at a sensitivity exceeding the sensitivity for the detection of carbon monoxide by a factor of about 5 and that for the detection of methane by a factor of about 20. The left center sensor element is composed of tin dioxide containing about 1% rhodium and is heated to an operating temperature of about 260° C. Under these conditions hydrogen is detected at a sensitivity which is about twice the sensitivity for detecting carbon monoxide and about 100 times the sensitivity for detecting methane. The right center sensor element is composed of tin dioxide containing 1% palladium and is heated to an operating temperature of about 360° C. Under these conditions hydrogen is detected at a sensitivity which is about twice the sensitivity for detecting carbon monoxide and about 10 times the sensitivity for detecting methane. The right-hand sensor element 5 is composed of titanium dioxide containing about 2% palladium and is heated to an operating temperature of about 360° C. Under these conditions the sensitivity for detecting hydrogen is about 200 times the sensitivity for detecting carbon monoxide and about 150 times the sensitivity for detecting methane. The output signals generated by the sensor elements 5 are fed to the evaluation device or circuit arrangement 100 and the signals are thereby processed and evaluated in conventional manner on the basis of regression analysis in order to yield the individual concentration data of hydrogen, carbon monoxide and methane.

In the event that one of the sensor elements 5 is intended to be sensitive to a number of components of the gas mixture to be investigated, i.e. in the case that an interfering gas is present, the sensitivity of one sensor element 5 can be adjusted such that this sensor element 5 responds to the interfering gas. In such a case the evaluation device or circuit arrangement 100 can be designed in such a manner that the concentration of the interfering gas is eliminated by computation so that the desired component of the gas mixture can be determined.

Figure 3:
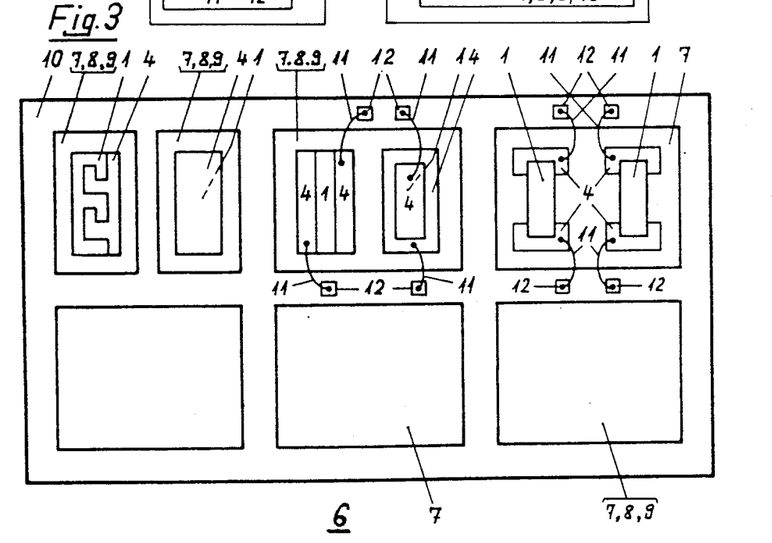
FIG. 3 is a top plan view of a gas sensor used in a second embodiment of the device according to the invention.

FIG. 3 is a top plan view of a second embodiment of the device according to the invention. In the gas sensor 6 used in this embodiment different sensor elements 5 are shown in individual regions in order to explain the multitude of possible arrangements. For better overview the sensor elements 5 have been shown only in the upper row of FIG. 3.

On the right in the upper row of FIG. 3 there is shown a structure in which no heating device is provided since the related sensor elements are operated at room temperature. Therefore, a second electrically insulating layer 9 is dispensed with and a first electrically insulating layer 7 can substrate 10. Electric conductors 11 connect electrodes 4 to electric contact points 12 which are also mounted at the substrate 10. Electric connecting wires which are not shown extend from the contact points 12 to an appropriate evaluation device or circuit arrangement.

Further structures of the sensor elements 5 having, for example, differently shaped electrodes 4 are shown in the upper row of FIG. 3. In the structure shown at the center of this upper row there is located below a first electrically insulating layer 7 a heating device or heating layer 8 which is common to a preselected number, specifically two, of sensor elements 5, and also a second electrically insulating layer 9 which is mounted at a heat-resistant, thermally insulating substrate 10. The two sensor elements 5 are heated to the same operating temperature in this case and are maintained at that temperature. The adaptation of the sensor elements' sensitivity for determining different components of gas mixtures is achieved by using different constituent materials 1 for the sensor elements 5.

A further structure of the sensor elements 5 is shown on the left in the upper row of FIG. 3. In this structure each sensor element 5 comprises a related heating device or heating layer 8 and, therefore, there are also provided individual first and second electrically insulating layers 7 and 9. The heating devices or layers 8 in the entire arrangement preferably are of the type described with reference to FIG. 2. The structure of the remaining components is as described hereinbefore, i.e. the sensor elements 5 are located on a heat-resistant, thermally insulating substrate 10, the electrical conductors 11 and the contact points 12 are, in turn, connected to an appropriate evaluation device or circuit arrangement by connecting wires not shown.

Twelve different gases can be detected using the gas sensor 6 illustrated in FIG. 3. The number of sensor elements 5 can be adapted to the number of components to be determined in the gas mixtures, i.e. this number can be greater or smaller than twelve.

Figure 4:
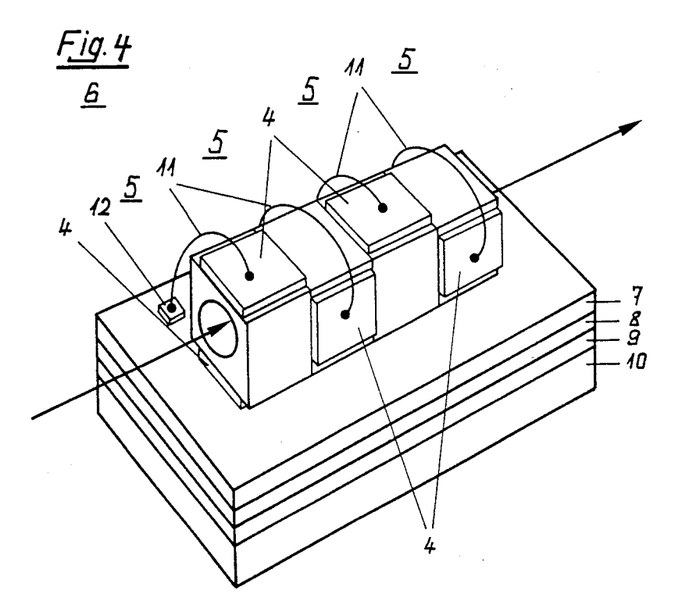
FIG. 4 is a perspective view of a gas sensor used in a third embodiment of the device according to the invention.

A third embodiment of the device according to the invention is illustrated in FIG. 4 and contains a different gas sensor 6. Several sensor elements 5 have the form of a cube with a central hole which extends through all of the sensor elements 5 and forms a tube. The gas or air to be investigated is conducted through this tube and exits from the end of the tube. The direction of flow is indicated by arrows. Each of the sensor elements 5 experiences a change in its electric conductivity when a predetermined gas flows past its 5 comprises electrodes 4 arranged in such a manner that they do not affect each other not withstanding the compact arrangement of the sensor elements 5. Electric conductors 11 connect the electrodes 4 to contact points 12 which are mounted at a first electrically insulating layer 7 and which are connected to an appropriate evaluation device or circuit arrangement. A heating device 8, preferably of the type as described hereinbefore with reference to FIG. 2, is arranged between the first and second electrically insulating layers 7 and 9 and heats the sensor elements 5 to the same operating temperature. The aforementioned arrangement is glued or adhesively bonded to a heat-resistant, thermally insulating substrate 10. More than only four gases can be detected using the gas sensor shown in FIG. 4 provided that the gas sensor 6 comprises a correspondingly greater number of sensor elements 5. The sensor elements 5 can also be operated in accordance with an optical measuring method and they can also be electrically insulated from each other by thin layers of an appropriate material.

The entire block which is formed by the sensor elements 5 is enclosed, with the exception of related openings at the two ends, by a gas-tight enclosure which is not shown in FIG. 4. It is thus possible to conduct a directed gas flow through the series-arranged sensor elements 5. The gaseous components of a gas mixture which are specifically consumed at the first sensor element 5 and generate thereat an electric signal, do not generate any further signals at the following sensor elements 5. Gaseous components which only react at the second sensor element 5 and generate thereat an electric signal, do not generate any signals at the following sensor elements and so forth. It is possible by such an arrangement to detect the components of a gas mixture at the separate sensor elements 5 by a change in the resistance thereof.

The electrodes 4 as shown in FIG. 4 do not have to be absolutely attached to the outside of the sensor elements 5, but can also be provided between the individual sensor elements.

For an even better separate investigation of the components of the gas mixture, for example, for the separate determination of gaseous contaminants in air, the gas sensor 6 shown in FIG. 4 advantageously can have a lower temperature at one end, for example, at the inlet opening than at the outlet opening. The sensor elements are thus arranged in a series which contains a forwardly positioned sensor element and a sensor element positioned rearwardly thereof in the gas flow direction and the forwardly positioned sensor element has a lower operating temperature than the sensor element positioned rearwardly thereof. Gases which already burn up at low temperatures will then preferably burn up at the first sensor element 5 and produce thereat a large change in the electric signals indicating the conductivity thereof. Gases which burn up only at higher temperatures will burn up at the second sensor element 5 and gases which burn up at still higher temperatures will only burn up at the third sensor element and so forth. The gases thus can be detected still much more selectively.

In the event that the sensor elements consist of a highly porous metal oxide gel like, for example, an aerogel, the central hole is not even necessary. The embodiment illustrated in FIG. 4 is intended to also include such cases.

Figure 5:
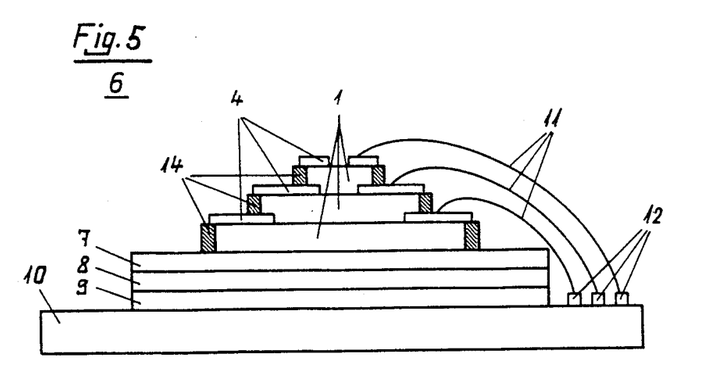
FIG. 5 is a side view of a gas sensor used in a fourth embodiment of the device according to the invention.

A gas sensor 6 used in a fourth embodiment of the inventive device is shown in FIG. 5 and is composed of a number of sensor elements 5 assembled in a pyramid shape. Electrodes 4 thereof are connected via electric conductors 11 to electric contact points 12 which, in turn, are mounted at a heat-resistant, thermally insulating substrate 10. The contact points 12 are here again connected to an appropriate evaluation device or circuit arrangement by connecting lines. The electrodes 4 are insulated in such a manner that they contact only the constituent material 1 of an associated sensor element 5 but not the constituent material 1 of a different sensor element 5. The outer walls of the sensor elements 5 are partially provided with a gas-impervious coating or layer 14. Therefore only the top surfaces of the sensor elements 5 interact with a gas or gas mixture. The sensor elements 5 are mounted at a first electrically insulating layer 7 which is connected to an electric heating device 8 preferably of the type as described with reference to FIG. 2 and to a second electrically insulating layer 9. The entire arrangement is mounted at a heat-resistant thermally insulating substrate 10.

The individual sensor elements 5 in this arrangement are heated to the same operating temperature. Due to the use of different constituent materials 1 each sensor element 5 is sensitized so as to respond to a predetermined component of the gas mixture to be investigated. There exists also the possibility of operating, for example, the top sensor element 5 at room temperature. In that case the top sensor element 5 is thermally insulated from the other sensor elements 5. Furthermore, a greater number of sensor elements 5 can be used in the gas sensor 6 of this embodiment than the number shown in FIG. 5.

In the embodiments as illustrated by FIGS. 2 to 5 the contact points 12 do not have to be absolutely located at the first electrically insulating layer 7 but may also be placed outside thereof.

Figure 6:
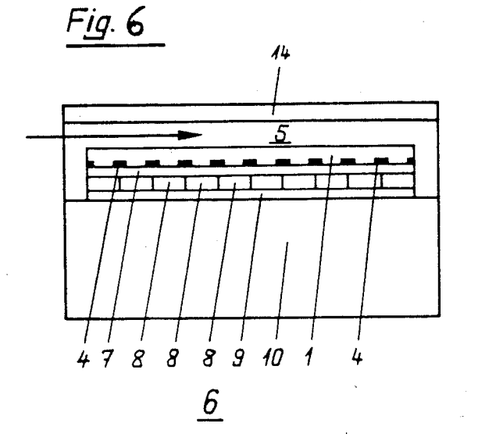
FIG. 6 is a longitudinal section through a gas sensor used in a fifth embodiment of the device according to the invention and including means for conducting a directed flow of the gas mixture past the sensor elements of the gas sensor.
Figure 7:
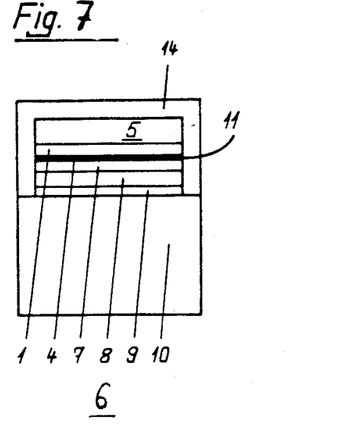
FIG. 7 is a cross-section through the gas sensor shown in FIG. 6.

A fifth embodiment of the inventive device which incorporates a differently structured gas sensor 6 is illustrated in FIGS. 6 and 7 in longitudinal section and in cross-section, respectively. The gas sensor 6 constitutes a combination or coherent block of a number of sensor elements which comprise a uniform constituent material 1. On the bottom side this constituent material 1 is provided with a large number of electrodes 4. The block of sensor elements 5 is mounted to a multiple number of heating devices 8, preferably of the type as described with reference to FIG. 2, by means of a common first electrically insulating layer 7. The heating device 8 at the full left in FIG. 6 heats the zone of the block of sensor elements which is located thereabove to a temperature of, for example, about 80° C. The next-following electric heating device 8 to the right thereof heats the zone of the block of sensor elements located thereabove to a temperature of, for example, about 90° C. and so forth. The block of sensor elements, therefore, has a temperature gradient which increases from the left towards the right. The individual heating devices 8 are mounted at a common thermally insulating substrate 10 by means of a common second electrically insulating layer 9.

The embodiment shown in FIGS. 6 and 7 comprises a gas sensor 6 with a gas-impervious layer 14 which encloses the common first electrically insulating layer 7, the heating devices 8 and the common second electrically insulating layer 9 as well as the block of sensor elements 5 such that a free space remains above the block. The gas or air to be investigated is passed through this free space from the left towards the right in a directed flow as indicated by the arrow in FIG. 6. This gas or air flow may be generated by means of a suitable pump which is not particularly illustrated or by vertically positioning the entire gas sensor 6 such that the heating device 8 associated with the lowest temperature is located at the bottom. The gas or air flow will be automatically adjusted in the last mentioned arrangement due to the stack effect.

FIG. 7 also shows electric conductors 11 leading to a suitable evaluation device or circuit arrangement through the gas-impervious layer 14.

The block of sensor elements thus is operable at a positive temperature gradient in the direction of the gas flow. Readily oxidizable gases will burn up already at the full left at low temperature and produce large changes in the electrical resistance in this region of the block of sensor elements. Gases which are more difficultly oxidized, for example, will only burn up in the region of the center of the block of sensor elements at a medium temperature and produce a large change in the electrical resistance in this region of the block of sensor elements. Very difficultly oxidizable gases, however, will only react at the right-hand, hot end of the block of sensor elements and cause a change in the resistance in this region of the block of the sensor elements. Due to this arrangement a gas mixture is thus separately investigated with respect to its components and these components are separately or individually detected. A very high selectivity of the gas sensor 6 is thereby achieved which can be considerably further increased by a suitable mathematical evaluation of the signals originating from the individual regions of the block of sensor elements. Such evaluation is performed in the evaluation device or circuit arrangement.

Figure 8:
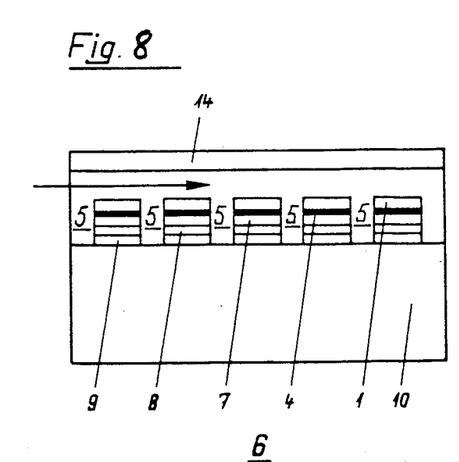
FIG. 8 is a longitudinal section through a gas sensor used in a sixth embodiment of the device according to the invention and including means for conducting a directed flow of the gas mixture past the sensor elements of the gas sensor.
Figure 9:
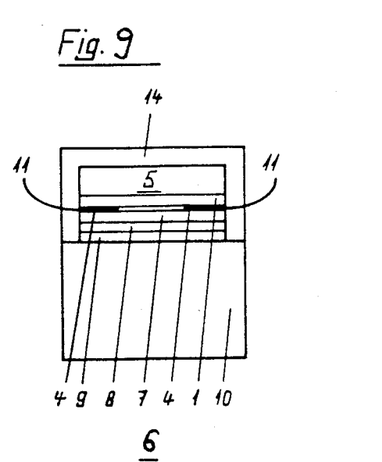
FIG. 9 is a cross-section through the gas sensor shown in FIG. 8.

A sixth embodiment of the device according to the invention contains another type of gas sensor 6 which is shown in FIGS. 8 and 9 in longitudinal section and in cross-section, respectively. The gas sensor 6 of this embodiment contains a number of series-arranged sensor elements 5 which are composed of different constituent materials 1 and each of which contains two electrodes 4. These sensor elements 5 are heated to individual operating temperatures by separate heating devices or layers 8 which preferably are of the type as described with reference to FIG. 2. The heating devices or layers 8 are located intermediate first and second electrically insulating layers 7 and 9 which are mounted to a common heat insulating substrate 10. Thus the sensor element 5 located at the full left has an operating temperature of, for example, only about 65° C. The next-following sensor element 5 located to the right thereof has an operating temperature of about 80° C. The next-following sensor element 5 has an operating temperature of about 100° C. and so forth. The sensor element 5 located at the full right has an operating temperature of about 400° C.

FIGS. 8 and 9 also illustrate a gas sensor 6 with a gas-impervious layer 14 which encloses the first electrically insulating layer 7, the electric heating devices 8 and the second electrically insulating layer 9 as well as the sensor elements 5 in such a manner that a free space remains above the sensor elements 5. The gas or air to be investigated is passed through this free space from the left to the right as indicated by the arrow in FIG. 8. As already explained with reference to FIG. 6 this, preferably laminar, gas or air flow can be generated either by an external pump or by the stack effect which is produced when the entire gas sensor 6 is vertically positioned such that the sensor element 5 having the lowest temperature is located at the bottom.

Electric conductors 11 shown in FIG. 9 lead through the gas-impervious layer 14 to a suitable evaluation device or circuit arrangement.

In the gas sensor 6 shown in FIGS. 8 and 9 readily oxidizable gases also will burn up already at the first sensor element 5 located at the full left and produce thereat a large change in the electrical resistance. The constituent material 1 of the sensor element 5 also is selected such, for example, by incorporating therein a specific catalyst, that the readily oxidizable substances preferably burn-up at this sensor element 5. This oxidation is strongly assisted by an optimum operating temperature which is somewhat lower than the operating temperature of the next-following sensor element 5 and by an appropriate chemical composition of the constituent material 1. Since in addition to increasing temperatures in the direction of the gas or air flow the chemical composition of the constituent materials 1 of the sensor elements is also selected with the view of obtaining an optimum performance, the gaseous components of the gas mixture or, for example, gaseous contaminants in air can be extremely selectively detected. The selectivity of this gas sensor 6 can be further increased to a large extent by a suitable mathematical combination of the signals originating from the individual sensor elements 5.

While there are shown and described present preferred embodiments of the invention, it is to be distinctly understood that the invention is not limited thereto, but may be otherwise variously embodied and practiced within the scope of the following claims.

Accordingly, what I claim is:

1. A device for selectively determining components of gas mixtures by means of a gas sensor, said device comprising:
   a predetermined number of sensor elements which change their properties under the action of the to-be-determined components of a gas mixture to be investigated;
   a heat resistant and thermally insulating substrate;
   said predetermined number of sensor elements being mounted at said heat resistant and thermally insulating substrate and thereby are thermally insulated from each other and can be heated to related operating temperatures independent of each other;
   said sensor elements being selected and operated such as to permit the determination of different ones of the components of said gas mixture; and an evaluation circuit arrangement operatively connected to said sensor elements in order to detect and evaluate the changes in the properties of said sensor elements under the action of the to-be-determined components of the gas mixture.

2. The device as defined in claim 1, wherein:
said property of said sensor elements which changes under the action of the to-be-determined components of the gas mixture and the change of which are detected by said evaluation circuit arrangement is the electric conductivity of the sensor elements.

3. The device as defined in claim 1, wherein:
each one of said predetermined number of sensor elements is selected on the basis of its constituent material in order to respond to a different one of the gaseous components present in the gas mixture.

4. The device as defined in claim 1, wherein:
each one of said predetermined number of sensor elements is selected on the basis of its operating temperature in order to respond to a different one of the gaseous components present in the gas mixture.

5. The device as defined in claim 1, wherein:
each one of said predetermined number of sensor elements is selected on the basis of its constituent material and its operating temperature in order to respond to a different one of the gaseous components present in the gas mixture.

6. The device as defined in claim 1, wherein:
each said sensor element of said predetermined number of sensor elements is provided with:
an electric heating device;
a first electrically insulating layer;
a second electrically insulating layer; and
said electric heating device being disposed between said first and second electrically insulating layers.

7. The device as defined in claim 6, wherein:
said electric heating device comprises a platinum layer having a large temperature coefficient of electric conductivity and serving to heat said sensor element and to determine the heating temperature thereof.

8. The device as defined in claim 6, wherein:
said electric heating device comprises an iridium layer having a large temperature coefficient of electric conductivity and serving to heat said sensor element and to determine the heating temperature thereof.

9. The device as defined in claim 6, wherein:
said electric heating device comprises a layer constituted by a platinum-iridium alloy; and
said platinum-iridium alloy layer having a large temperature coefficient of electric conductivity and serving to heat said sensor element and to determine the heating temperature thereof.

10. The device as defined in claim 1, wherein:
a preselected number of said predetermined number of sensor elements is provided with:
an electric heating device;
a first electrically insulating layer;
a second electrically insulating layer; and
said electric heating device being disposed between said first and second electrically insulating layers.

11. The device as defined in claim 10, wherein:
said electric heating device comprises a platinum layer having a large temperature coefficient of electric conductivity and serving to heat said preselected number of sensor elements and to determine the heating temperature thereof.

12. The device as defined in claim 10, wherein:
said electric heating device comprises an iridium layer having a large temperature coefficient of electric conductivity and serving to heat said preselected number of sensor elements and to determine the heating temperature thereof.

13. The device as defined in claim 10, wherein:
said electric heating device comprises a layer constituted by a platinum-iridium alloy; and
said platinum-iridium alloy layer having a large temperature coefficient of electric conductivity and serving to heat said preselected number of sensor elements and to determine the heating temperature thereof.

14. The device as defined in claim 1, wherein:
said predetermined number of sensor elements is provided with:
a common electric heating device;
a first electrically insulating layer and a second electrically insulating layer; and
said common electric heating device being disposed between said first and said second electrically insulating layers.

15. The device as defined in claim 14, wherein:
said electric heating device comprises a platinum layer having a large temperature coefficient of electric conductivity and serving to heat said predetermined number of sensor elements and to determine the heating temperature thereof.

16. The device as defined in claim 14, wherein:
said electric heating device comprises an iridium layer having a large temperature coefficient of electric conductivity and serving to heat said predetermined number of sensor elements and to determine the heating temperature thereof.

17. The device as defined in claim 14, wherein:
said electric heating device comprises a layer constituted by a platinum-iridium alloy; and
said platinum-iridium alloy layer having a large temperature coefficient of electric conductivity and serving to heat said predetermined number of sensor elements and to determine the heating temperature thereof.

18. The device as defined in claim 1, further including:
means for conducting a directed flow of said gas mixture to be investigated along said predetermined number of sensor elements.

19. The device as defined in claim 18, wherein:
said sensor elements constituting said predetermined number of sensor elements are series-arranged with respect to the direction of said directed flow of said gas mixture to be investigated.

20. The device as defined in claim 19, wherein:
said sensor elements constituting said predetermined number of sensor elements form a coherent block of sensor elements.

21. The device as defined in claim 20, further including:
a predetermined number of electrodes provided for said coherent block of sensor elements.

22. The device as defined in claim 19, further including:

means for heating each one of said series-arranged sensor elements to a selected operating temperature.

23. The device as defined in claim 1, further including:
   a gas-impervious layer; and
   said gas-impervious layer being arranged such that said gas mixture to be investigated is guided in a directed flow past said predetermined number of sensor elements.

24. The device as defined in claim 23, wherein:
   said sensor elements constituting said predetermined number of sensor elements are series-arranged with respect to the direction of said directed flow of said gas mixture to be investigated.

25. The device as defined in claim 24, wherein:
   said sensor elements constituting said predetermined number of sensor elements form a coherent block of sensor elements.

26. The device as defined in claim 25, further including:
   a predetermined number of electrodes provided for said coherent block of sensor elements.

27. The device as defined in claim 24, further including:
   means for heating each one of said series-arranged sensor elements to a selected operating temperature.

28. A device for selectively determining components of gas mixtures by means of a gas sensor, said device comprising:
   a predetermined number of sensor elements which change their properties under the action of the to-be-determined components of a gas mixture to be investigated;
   a heat resistant and thermally insulating substrate on which said predetermined number of sensor elements is arranged;
   said sensor elements being selected and operated such as to permit the determination of different ones of the components of said gas mixture;
   an evaluation circuit arrangement operatively connected to said sensor elements in order to detect and evaluate the changes in the properties of said sensor elements under the action of the to-be-determined components of the gas mixture;
   means for conducting a directed flow of said gas mixture to be investigated along said predetermined number of sensor elements;
   said sensor elements constituting said predetermined number of sensor elements being series-arranged with respect to the direction of said directed flow of said gas mixture to be investigated;
   said sensor elements constituting said predetermined number of sensor elements forming a coherent block of sensor elements; and
   means for operating said sensor elements at a temperature gradient in the direction of said directed flow of said gas mixture to be investigated.

29. A device for selectively determining components of gas mixtures by means of a gas sensor, said device comprising:
   a predetermined number of gas sensor elements which change their properties under the action of the to-be-determined components of a gas mixture to be investigated;
   a heat resistant and thermally insulating substrate on which said predetermined number of sensor elements is arranged;
   said sensor elements being selected and operated such as to permit the determination of different ones of the components of said gas mixture;
   an evaluation circuit arrangement operatively connected to said sensor elements in order to detect and evaluate the changes in the properties of said sensor elements under the action of the to-be-determined components of the gas mixture;
   means for conducting a directed flow of said gas mixture to be investigated along said predetermined number of sensor elements;
   said sensor elements constituting said predetermined number of sensor elements being series-arranged with respect to the direction of said directed flow of said gas mixture to be investigated;
   means for heating each one of said series-arranged sensor elements to a selected operating temperature;
   said series-arranged sensor elements containing a forwardly positioned sensor element and a sensor element positioned rearwardly thereof relative to said direction of the directed flow of said gas mixture to be investigated; and
   said forwardly positioned sensor element having a lower operating temperature than said sensor element positioned rearwardly thereof.

30. A device for selectively determining components of gas mixtures by means of a gas sensor, said device comprising:
   a predetermined number of sensor element which change their properties under the action of the to-be-determined components of a gas mixture to be investigated;
   a heat resistant and thermally insulating substrate on which said predetermined number of sensor elements is arranged;
   said sensor elements being selected and operated such as to permit the determination of different ones of the components of said gas mixtures;
   an evaluation circuit arrangement operatively connected to said sensor elements in order to detect and evaluate the changes in the properties of said sensor elements under the action of the to-be-determined components of the gas mixture;
   a gas-impervious layer;
   said gas-impervious layer being arranged such that said gas mixture to be investigated is guided in a directed flow past said predetermined number of sensor elements;
   said sensor elements constituting said predetermined number of sensor elements being series-arranged with respect to the direction of said directed flow of said gas mixture to be investigated;
   said sensor elements constituting said predetermined number of sensor elements forming a coherent block of sensor elements; and
   means for operating said sensor element at a temperature gradient in the direction of said directed flow of said gas mixture to be investigated.

31. A device for selectively determining components of gas mixtures by means of a gas sensor, said device comprising:
   a predetermined number of sensor elements which change their properties under the action of the to-be-determined components of a gas mixture to be investigated;

a heat resistant and thermally insulating substrate on which said predetermined number of sensor elements is arranged;

said sensor elements being selected and operated such as to permit the determination of different ones of the components of said gas mixture;

an evaluation circuit arrangement operatively connected to said sensor elements in order to detect and evaluate the changes in the properties of said sensor elements under the action of the to-be-determined components of the gas mixture;

a gas-impervious layer;

said gas-imprevious layer being arranged such that said gas mixture to be investigated is guided in a directed flow past said predetermined number of sensor elements;

said sensor elements constituting said predetermined number of sensor elements being series-arranged with respect to the direction of said direction flow of said gas mixture to be investigated;

means for heating each one of said series-arranged sensor elements to a selected operating temperature;

said series-arranged sensor elements containing a forwardly positioned sensor element and a sensor element positioned rearwardly thereof relative to said direction of the directed flow of the gas mixture to be investigated; and said forwardly positioned sensor element having a lower operating temperature than said sensor element positioned rearwardly thereof.

* * * * *

UNITED STATES PATENT AND TRADEMARK OFFICE
CERTIFICATE OF CORRECTION

PATENT NO. : 4,584,867
DATED : Apr. 29, 1986
INVENTOR(S) : Martin Forster

It is certified that error appears in the above—identified patent and that said Letters Patent is hereby corrected as shown below:

Column 1, line 68, after "for" insert --example, in kitchens and so forth, and the interference is due--

Column 4, line 19, after "In" insert --such case there can be simultaneously determined the heating--

Column 5, line 50, after "end" insert --of the arrangement is composed of tin dioxide containing about--

Column 6, line 36, after "can" insert --be directly mounted at a heat-resistant, thermally insulating--

Column 6, line 67, after "the" insert --electrodes 4 are connected to electric contact points 12 by--

Column 7, line 17, after "its" insert --surface with respect to which gas the response properties of the sensor element 5 have been optimized. Each sensor element--

UNITED STATES PATENT AND TRADEMARK OFFICE
CERTIFICATE OF CORRECTION

PATENT NO. : 4,584,867
DATED : April 29, 1986
INVENTOR(S) : Martin Forster

It is certified that error appears in the above-identified patent and that said Letters Patent is hereby corrected as shown below:

Column 14, line 34, delete "element" and insert --elements--
Column 15, line 17, delete "gas-imprevious" and insert --gas-impervious--

Signed and Sealed this

Twenty-sixth Day of August 1986

[SEAL]

Attest:

DONALD J. QUIGG

Attesting Officer   Commissioner of Patents and Trademarks